United States Patent [19]

Morris et al.

[11] Patent Number: 4,827,060
[45] Date of Patent: May 2, 1989

[54] REMOVAL AND RECYCLING OF CATALYSTS IN CHLORINATED PROCESS STREAMS

[75] Inventors: Thomas E. Morris; Rae L. Spencer; Gerald A. Gimber, all of Lake Jackson, Tex.

[73] Assignee: The Dow Chemical Company, Midland, Mich.

[21] Appl. No.: 118,703

[22] Filed: Nov. 9, 1987

[51] Int. Cl.$^4$ .................... C07C 17/08; C07C 17/02; C07C 17/38; B01J 27/32
[52] U.S. Cl. ............................. 570/250; 423/140; 423/141; 423/122; 502/24; 570/248; 570/254; 570/262
[58] Field of Search ............ 502/24, 22, 20, 56; 423/140, 141, 493; 570/262, 235, 238, 250, 254

[56] References Cited

U.S. PATENT DOCUMENTS

| | | | |
|---|---|---|---|
| 2,225,933 | 12/1940 | Slotterbeck | 570/250 |
| 3,115,528 | 12/1963 | Benner, Jr. et al. | 260/652 |
| 3,420,749 | 1/1969 | Dehn | 203/6 |
| 3,654,093 | 4/1972 | Schexnayder et al. | 203/8 |
| 3,846,253 | 11/1974 | Obrecht | 203/7 |
| 3,848,005 | 11/1974 | Sullivan | 260/625.5 |
| 4,307,261 | 12/1981 | Beard, Jr. et al. | 520/262 |
| 4,412,086 | 10/1983 | Beard, Jr. et al. | 570/262 |
| 4,533,473 | 8/1985 | Burks, Jr. et al. | 210/754 |
| 4,614,643 | 9/1986 | Doahe | 570/262 |
| 4,649,201 | 3/1987 | Friese | 423/493 |

FOREIGN PATENT DOCUMENTS

| | | |
|---|---|---|
| 702594 | 1/1965 | Canada ............ 570/250 |
| 530877 | 1/1977 | Canada . |
| 2069489 | 8/1981 | Canada . |
| 3247988A | 6/1984 | Canada . |
| 146882A | 7/1985 | Canada . |

*Primary Examiner*—Paul E. Konopka
*Attorney, Agent, or Firm*—Paula Sanders Ruhr

[57] ABSTRACT

A catalyst, such as FeCl$_3$, useful in the production of chlorinated hydrocarbons such as 1,1-dichloroethane is removed from the effluent of a process reactor and recycled. Hydrochloric acid is removed from the process stream resulting in the catalyst present in the process stream in solution precipitating out of solution. Then it can be removed from the process stream by conventional separation techniques. Alternatively, the catalyst present in the process stream as a solid, without the removal of HCl, is separated from the liquid present by means of a cyclone and recycled. In both cases, the catalyst retains its catalytic activity.

23 Claims, 1 Drawing Sheet

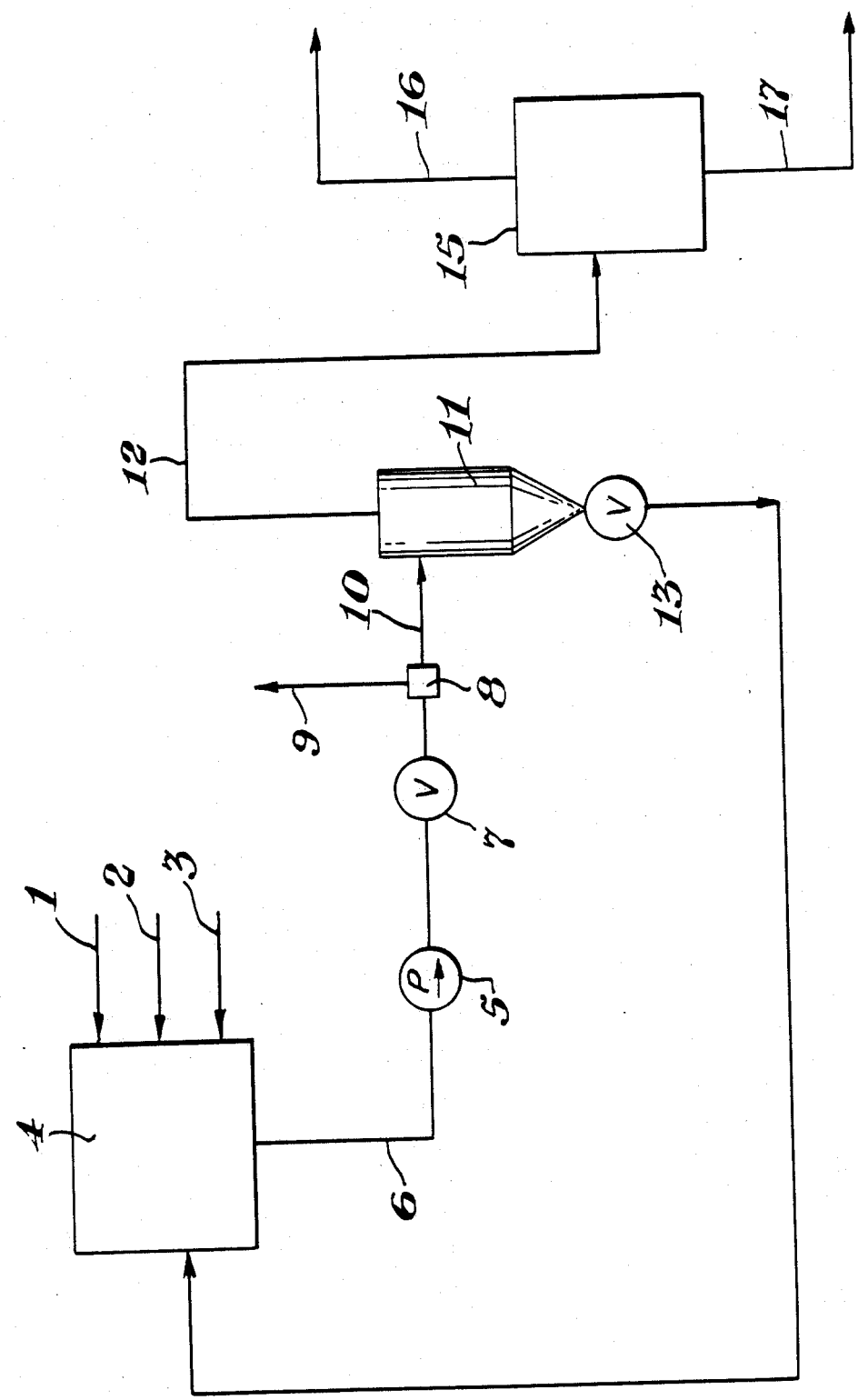

4,827,060

REMOVAL AND RECYCLING OF CATALYSTS IN CHLORINATED PROCESS STREAMS

BACKGROUND OF THE INVENTION

This invention relates to the treatment of chlorinated hydrocarbon process streams to remove and recycle metallic impurities such as ferric iron.

Chlorinated hydrocarbons possess various utilities as, for example, solvents and pesticides and as intermediates in organic synthesis.

A number of valuable chlorinated hydrocarbons such as 1,1-dichloroethane, 1,2-dichloroethane, 1,1,2,2-tetrachloroethane, and 1,1,1-trichloroethane, ethyl chloride and analogous chlorinated derivatives of higher hydrocarbons such as propane or butane are commonly made by liquid phase catalytic hydrochlorination or chlorination of the corresponding unsaturated precursor such as ethylene, vinyl chloride or vinylidene chloride. Metallic halides, particularly ferric chloride, are often the catalysts in these processes. However, the removal of ferric iron or other metallic contaminants that result from the use of these catalysts has been a long-standing problem. The presence of metalic ions, particularly in the form of ferric chloride catalysts, during the flashing and recovery of the desired chlorinated hydrocarbons causes dehydrochlorination of the desired chlorinated hydrocarbons and subsequent polymerization of the resulting unsaturated products. This results in the production of tars which must be disposed of as hazardous wastes.

Various techniques have been proposed to remove the ferric iron or other metallic contaminants from chlorinated hydrocarbon process streams. Soviet Union Pat. No. 530,877 discloses the use of a reducing agent such as reduced iron, stannous chloride, or cuprous chloride to reduce Fe(III) to Fe(II) to facilitate the precipitation of the iron. U.S. Pat. No. 4,533,473 describes the removal of metallic contaminants by contacting the process stream with a dilute aqueous solution of a mineral acid in which the contaminant is generally soluble. The contaminant can then be removed with the dilute mineral acid. Other patents, such as U.S. Pat. No. 4,412,086 and U.S. Pat. No. 4,307,261, describe the use of hydrocarbon oils which are less volatile than the desired products and in which ferric iron is less soluble to separate the ferric iron from the desired products. The more volatile hydrocarbons are removed by flashing or fractional distillation and the iron and less volatile oils are left behind. The iron is not soluble in the remaining hydrocarbon oil and precipitates out and can then be separated.

These techniques are not without problems. The catalyst recovered generally has lost most or all of its catalytic activity. Further, the processes necessary to remove the iron or other catalysts frequently require multiple steps and the building and maintenance of special equipment. Thus, what is needed is a method of removing the ferric iron or other metallic contaminants from chlorinated hydrocarbon process streams that is simple, efficient and economical and that retains the iron in a form with its catalytic activity either unchanged or minimally changed so that the catalyst may be recycled.

SUMMARY OF THE INVENTION

The present invention is such a process for the recycling of a catalyst, useful in reactions for the production of chlorinated hydrocarbons, which is present in a liquid process stream with the chlorinated hydrocarbon products and other components, comprising
 (a) separating the catalyst present as a solid from the liquid process stream; and
 (b) returning the separated catalyst to the process reactor.

It is surprising that the activity of the catalyst is not affected to a significant extent by this process.

BRIEF DESCRIPTION OF THE DRAWING

The drawing labeled FIG. 1 illustrates in schematic a preferred embodiment of the process of this invention whereby a $FeCl_3$ catalyst is removed from a process stream and recycled.

DETAILED DESCRIPTION OF ILLUSTRATIVE EMBODIMENTS

In a preferred embodiment of this invention, the process stream component in which the catalyst is most soluble in removed from the process stream prior to separating the solid catalyst from the liquid process stream. The removal of this process stream component results in the separation of a larger portion of the catalyst from the liquid process stream.

The present invention may be used in any process for the production of chlorinated hydrocarbons which has the following characteristics:
 (1) a liquid process stream is present;
 (2) said process stream is contaminated with a Friedel-Crafts catalyst such as $FeCl_3$ or $AlCl_3$;
 (3) said catalyst, if soluble, is soluble in a component of the process stream other than the desired product; and
 (4) said component can be removed from the process stream without removing the desired product.

Examples of such processes include the preparation of 1,2-dichloroethane from ethylene and chlorine; the preparation of 1,1-dichloroethane from vinyl chloride and HCl; the preparation of 1,1,2,2-tetrachloroethane from ethylene and HCl; the preparation of ethyl chloride from ethylene and HCl; and the preparation of 1,1,1-trichloroethane.

The precise characteristics of the process for the preparation of the chlorinated hydrocarbons are not crucial to the practice of this invention and will change depending on the particular chlorinated hydrocarbon being produced. The liquid process stream from which the catalyst is removed may be the effluent from the reactor of a single stage process or a multi-stage process. It may be at any temperature, pressure and rate of flow at which the process of the present invention may be practiced and the most preferred conditions will vary depending on the nature of the components of the process stream and on the reactor design and can be readily selected by one skilled in the art.

The catalyst to be removed from the process stream may be any Friedel-Crafts catalyst useful in the processes described herein. It is preferred that the catalyst be a metallic halide and more preferred that the catalyst be $AlCl_3$ or $FeCl_3$. In the most preferred embodiment of the invention, the catalyst is $FeCl_3$. The amount of catalyst that is present in a chlorinated hydrocarbon process stream will, of course, vary depending on the particular process being practiced. The process of this invention is effective for process streams containing any amount of catalyst from about 1 part per million (ppm)

by weight up to about 1 weight percent catalyst based on the weight of the reaction mixture. It is preferred that the catalyst be present in an amount of at least about 4 ppm by weight and no more than about 500 ppm by weight. It is more preferred that the catalyst be present at at least about 50 ppm and no more than about 100 ppm by weight.

The catalyst is normally not soluble in the reaction product, but is soluble in contaminants present in the process stream. Examples of such contaminants include HCl, which is present as a reactant or by-product, and water. In a preferred embodiment, HCl is the contaminant to be removed.

The removal of some or all of the contaminants in which the catalyst is at least partially soluble causes the catalyst to precipitate from the solution. The amount of contaminants to be removed from the process stream is any amount which will cause a sufficient portion of the catalyst to precipitate from the solution to reduce the amount of catalyst present in the tarpot to a sufficient level so that the amount of tars formed therein is significantly lowered. It is preferred that at least about 50 weight percent of the total contaminant is removed. It is more preferred that at least about 75 weight percent is removed and it is most preferred that at least about 90 weight percent of the total contaminant is removed.

In the process of this invention, the contaminants are removed from the liquid process stream by vaporizing the contaminants while leaving the desired product in the liquid phase. This can be accomplished by raising the temperature of the process stream, lowering the pressure of the process stream or a combination of both or by other separation techniques known to the art. It is preferred to vaporize the contaminants by rapidly lowering the pressure in the process stream. The pressure can be lowered any amount which will result in the contaminants being vaporized. It is preferred that the pressure be decreased to a pressure no more than 70 percent of the original pressure. It is more preferred that the pressure be decreased to a pressure no more than about 50 percent of the original pressure. It is most preferred that the pressure in the process stream be lowered to a pressure which is about 30 percent of the original pressure. This pressure decrease is preferably accomplished in a relatively short period of time. It is preferred that the pressure drop occur in no more than one second. It is more preferred that the pressure drop occur in less than 0.1 second. Any means for lowering the pressure that results in a pressure drop sufficient to vaporize the contaminants is operable in the practice of the process of this invention. Examples of suitable techniques include valves, restricting orifices, small piping or equipment such as heat exchangers. It is preferred to use a valve to lower the pressure.

The contaminants, after being vaporized, are removed from the process stream. The way in which the contaminants are removed is not critical so long as the contaminants leave the process stream while the desired products and the catalyst remain in the process stream. It is preferred to remove the contaminants by means of a vent and in such a way that the contaminants, if valuable, are not lost.

The pressure in the process stream as it leaves the reactor may be left unchanged or may be increased by pumping or other means prior to the removal and recycling of the catalyst by the practice of this invention. Similarly, the rate of flow in the process stream may be left unchanged or modified by pumping or other means prior to the removal and recycling of the catalyst by the practice of this invention. The practice of this invention does not require special pressure or pumping conditions other than that the conditions be such that the process stream is in the liquid phase and the contaminants may be selectively removed by vaporization. Within this limitation, the pressure and pumping conditions may be optimized to meet the requirements of the overall process for the preparation of the chlorinated hydrocarbons. It is preferred that the pressure be at least about 0 psig and no greater than about 100 psig.

Any temperature at which the components of the process stream, with the exception of the catalyst, are in the liquid phase and the contaminants in which the catalyst is most soluble may be vaporized is operable in the practice of this invention. The preferred temperature ranges will depend, at least in part, on the particular chlorinated hydrocarbon being produced and the process by which it is produced. It is most preferred that the temperature of the process stream be unchanged from what it would be in the absence of this invention. That is, it is most preferred that the process of recycling the catalyst be conducted at the temperature at which the process stream would normally exist.

Removal of the process stream contaminants in which the catalyst is most soluble causes the catalyst to precipitate out of solution. It is preferred that the catalyst originally be present both in solution and in colloidal form. Thus, when the catalyst in solution precipitates out of solution, it precipitates onto the colloidal catalyst already present and increases the size of the catalyst particles to a point where the catalyst can be removed from the process stream for returning to the process reactor for recycling by conventional techniques for the separation of solids and liquids. Examples of such methods include filtration, centrifugation and use of a cyclone. It is preferred to separate the solid from the liquid by means of a cyclone. The amount of catalyst removed from the process stream and recycled may be any amount which will reduce the catalyst present in the process stream so as to decrease the formation of tars in the tarpot by an amount essentially equal to the percent of catalyst removed. As an example, if 85 weight percent of the catalyst is removed, the formation of tars will be decreased by about 85 weight percent. It is preferred that at least about 50 percent on a weight basis of the catalyst is removed resulting in a decrease in tar formation of about 50 weight percent. It is more preferred that at least about 75 weight percent of the catalyst is removed resulting in a decrease in tar formation of about 75 weight percent and it is most preferred that at least about 90 percent is removed resulting in a decrease in tar formation of about 90 weight percent.

When the removal of less than about 50 weight percent of the catalyst will provide a satisfactory reduction in the formation of tars under process conditions, such removal may be obtained without the removal of the process stream component in which the catalyst is most soluble. Under many process conditions, some of the catalyst will be present in solid form and a significant portion of this catalyst may be removed by the practice of this invention. In particular, a significant portion of the catalyst may be removed by using a cyclone to separate the solid and the liquid. It is preferred that at least about 25 weight percent of the catalyst is removed without the removal of the process stream component in which the catalyst is most soluble. This results in a 25 weight percent decrease in tar formation. It is more preferred that at least about 35 weight percent is removed resulting in about a 35 percent decrease in tar formation and most preferred that at least about 50 weight percent is removed resulting in a decrease in tar formation of about 50 percent.

When the solid catalyst is separaed from the liquid process stream containing primarily the chlorinated hydrocarbon product, the amount of liquid going with the catalyst to be recycled may vary depending on the overall process requirements. It is preferred that the ratio of the liquid and solid catalyst being returned to the reactor for recycling to the liquid going on to the next stage of the process range from about 3:1 to about 1:12. It is more preferred that this ratio range from about 2:1 to about 1:3. It is most preferred that the ratio be about 1:1. The amount of liquid going with the catalyst to be recycled may be controlled by the use of a valve or choice of cyclone size. It is preferred that it be controlled by means of a valve.

The catalyst being recycled maintains a high degree of catalytic activity. It is preferred that the catalyst maintain at least about 50 percent of the activity it had prior to being separated from the process stream and returned to the reactor for recycling. It is more preferred that the catalyst maintain at least 75 percent of its activity and most preferred that it maintain at least about 90 percent of its activity.

A more thorough understanding of this invention may be obtained by reference to FIG. 1 which outlines a process for the liquid phase reaction of hydrogen chloride and vinyl chloride in the presence of a homogeneous $FeCl_3$ catalyst to form 1,1-dichloroethane. It should be noted that the figure refers to a preferred embodiment of the invention and is presented to offer a better understanding of it, but the figure should not be interpreted as limiting the invention in any way.

In FIG. 1, reactant streams 1 and 2 represent respectively the reactants, vinyl chloride and hydrogen chloride. Reactant stream 3 represents the catalyst, $FeCl_3$. The liquid phase reactor is represented by 4. The process stream 6 is the effluent from the reactor 4 and contains 1,1-dichloroethane, unreacted HCl and unreacted vinyl chloride, all in the liquid phase. $FeCl_3$ is also present both in solution and as colloidal iron. It is present at a level of approximately 500 ppm (parts per million). The rate of flow of process stream 6 is about 70 gallons per minute and its temperature is about 50° C. The pressure in the process stream 6 is increased to about 100 psig from the about 55 psig in the reactor 2 by means of a pump 5 in the process line 6. The pressure in the process stream 6 is rapidly reduced to about 35 psig by means of a valve 7 and HCl and vinyl chloride are removed from the process stream as vapors by means of a vent 8 through process line 9. This results in the removal of about 75 weight percent of HCl. Since the $FeCl_3$ is soluble in HCl and less soluble in 1,1-dichloroethane, this results in more than 95 percent on a weight basis of the $FeCl_3$ present in the solution precipitating out onto the colloidal iron already present. Process stream 10 now contains predominantly 1,1-dichloroethane and $FeCl_3$ and enters a cyclone 11 where at least about 50 percent of the $FeCl_3$ is removed as the bottoms and the overflow in process stream 12 of the cyclone 11 contains 1,1-dichloroethane, a small amount of $FeCl_3$, vinyl chloride and hydrogen chloride. The bottoms contain $FeCl_3$ and 1,1-dichloroethane which are recycled to the reactor 4 via process stream 14. The amount of 1,1-dichloroethane leaving the cyclone 11 as bottoms is controlled by a valve 13. The rate of flow of the process stream 14 containing the bottoms is about 5 to about 35 gallons per minute and its pressure and temperature are about 35 psig and about 55° C. respectively. The $FeCl_3$ recycled to the reactor 4 has virtually the same catalytic activity as fresh catalyst. The overflow stream 12 flows at a rate of about 65 gallons per minute. Its temperature is about 55° C. and its pressure is about 35 psig. The 1,1-dichloroethane, small amount of $FeCl_3$, vinyl chloride and hydrogen chloride in the overflow stream 12 enter a vessel 15 where the 1,1-dichloroethane is flashed overhead and removed in process stream 16 while the bottoms are removed through process stream 17 for disposal.

The following examples are given to illustrate the invention, but should not be interpreted as limiting it in any way. Unless stated otherwise, all parts and percentages given are by weight.

COMPARATIVE EXAMPLE 1

Determination of $FeCl_3$ Particle Size in Reactor Effluent (Not an embodiment of the invention)

Samples are taken from a 1,1-dichloroethane process stream feeding a tarpot by means of a sample line fitted with a Nupro ® sintered metal filter. Three filters are used, having 2, 7 and 15 micron pore sizes respectively. In each instance, approximately 20 ml of filtered liquid is run into a tared 2-ounce bottle. A weighed amount, approximately 75 g, of 0.1N HCl is added to the bottle, it is shaken for 10 minutes and the $FeCl_3$ is extracted into the aqueous phase. The sample is analyzed for iron by means of atomic absorption (AA). An unfiltered sample is simultaneously taken with each filtered sample and also analyzed for Fe by AA. The results obtained are presented in Table I below.

TABLE I

| Fe Remaining in Filtered vs. Non-Filtered Samples | | |
|---|---|---|
| Filter Size (microns) | Fe Content (ppm) | Fe Removal (%) |
| 2 | 89 | 28.9 |
| unfiltered | 125 | — |
| 7 | 123 | 6.1 |
| unfiltered | 131 | — |
| 15 | 113.5 | 9.2 |
| unfiltered | 125 | — |

The information in Table I shows that, untreated, the particle size of the iron is quite small and that even with a 2 micron filter, only about 28.9 percent of the iron can be removed by filtration.

EXAMPLE 1

Effect of Removal of HCl from Chlorinated Solvent Process Stream on the Particle Size of $FeCl_3$ Three unfiltered samples are taken from the process stream in the same manner as in Example 1 and analyzed for Fe by AA. Each sample is then allowed to stand with the bottle cap removed. A small nitrogen purge is placed on the head space to prevent the absorption of water from the atmosphere. HCl evolves from the solution as a vapor. At 15- and 75-minute intervals, the liquid in the bottles is sampled, filtered and analyzed for Fe by AA. Glass filters of 0.3 and 2.7 microns are used on the first two samples and a 5–10 micron filter paper is used on the last sample. The results of this experiment are shown in Table II below.

TABLE II

| Fe Removal After Degassing HCl | | | |
|---|---|---|---|
| Filter Size (microns) | Time (min) | Fe Content (ppm) | Fe Removal (%) |
| 0.3 | 0 | 65 | — |
| 0.3 | 15 | 2 | 97 |
| 0.3 | 75 | 6 | — |
| 2.7 | 0 | 146 | — |
| 2.7 | 15 | 16 | 89 |
| 2.7 | 75 | 37 | — |
| 5–10 | 0 | 125 | — |
| 5–10 | 15 | 25 | 80 |
| 5–10 | 75 | 60 | — |

The above data shows that, about 15 minutes after the degassing of HCl, the Fe content of the samples can be decreased by 97 percent by filtration through a 0.3 micron filter and by almost 90 percent when using a 2.7 micron filter. This shows that the removal of the HCl results in the particle size of iron increasing substantially so that it can be removed by conventional techniques. The increase in the amount of Fe present at 75 minutes is probably due to the absorption of some water from the atmosphere into the solution thus increasing the solubility of iron and decreasing the ease of removing it from the solution.

EXAMPLE 2

Removal of FeCl$_3$ Without removing HCl

In a process for the production of 1,1-dichloroethane, the reactor effluent containing 1,1-dichloroethane, FeCl$_3$, and HCl, at 50 psig and 24° C. is routed through a 10 mm cyclone. A 50 psi pressure drop is obtained across the cyclone and both the overflow and the underflow from the cyclone enter sample bottles at atmospheric pressure. The feed to the cyclone is 5.38 pounds/minute and the iron content as measured by atomic absorption is 116 ppm. The overflow from the cyclone is 2.51 pounds/minute and the iron content is 63 ppm. The underflow from the cyclone is 2.87 pounds/minute and the iron content is 146 ppm. This indicates that the amount of iron removed and recycled is 45.7 percent and the amount of 1,1-dichloroethane recycled is 53.3 percent.

What is claimed is:

1. A process for recycling a catalyst, selected from the group consisting essentially of AlCl$_3$ and FeCl$_3$, in a process for the production of chlorinated hydrocarbons wherein the catalyst, hydrochloric acid and a reactant selected from the group consisting essentially of chlorinated hydrocarbons and hydrocarbons are placed into a liquid phase reactor and a liquid process stream is produced which comprises the unreacted reactant, unreacted hydrochloric acid and chlorinated hydrocarbon product and is contaminated with the catalyst, present both in solution and in solid form, said recycling process consisting essentially of using a separating means to separate a portion of the liquid process stream containing an amount of the catalyst in solid form which constitutes at least about 50 weight percent of the total catalyst present in the liquid process stream from the remainder of the process stream and recycling the separated portion to the reactor wherein at least about 50 weight percent of the hydrochloric acid is removed from the liquid process stream prior to using the separating means to separate the portion of the liquid process stream containing the catalyst in solid form.

2. The process of claim 1 wherein the catalyst is FeCl$_3$.

3. The process of claim 1 wherein the HCl is removed from the process stream in the vapor phase.

4. The process of claim 3 wherein at least about 75 percent of the HCl is removed from the process stream.

5. The process of claim 4 wherein at least about 90 percent of the HCl is removed from the process stream.

6. The process of claim 3 wherein the pressure in the process stream is rapidly decreased causing the HCl to vaporize.

7. The process of claim 6 wherein the pressure in the process stream is rapidly decreased by means of a valve.

8. The process of claim 1 wherein at least about 75 weight percent of the catalyst is removed from the process stream.

9. The process of claim 8 wherein at least about 90 weight percent of the catalyst is removed from the process stream.

10. The process of claim 1 wherein the catalyst is removed from the process stream by means of a cyclone.

11. The process of claim 1 wherein the chlorinated hydrocarbon is 1,1-dichloroethane produced by the reaction of vinyl chloride and HCl in the presence of a FeCl$_3$ catalyst.

12. The process of claim 1 wherein the recycled FeCl$_3$ catalyst retains at least about 75 percent of its catalytic activity.

13. The process of claim 12 wherein the recycled FeCl$_3$ catalyst retains at least about 90 percent of its catalytic activity.

14. A process for the recycling of a catalyst, selected from the group consisting essentially of AlCl$_3$ and FeCl$_3$, in a process for the production of chlorinated hydrocarbons wherein the catalyst, a chlorinating agent and a reactant selected from the group consisting essentially of chlorinated hydrocarbons and hydrocarbons are placed into a liquid phase reactor and a liquid process stream is produced which comprises the unreacted reactant, unreacted chlorinating agent and chlorinated hydrocarbon product and is contaminated with the catalyst, present both in solution and in solid form, said recycling process consisting essentially of using a separating means to separate a portion of the liquid process stream containing an amount of the catalyst in solid form which constitutes at least about 25 weight percent of the total catalyst present in the liquid process stream from the remainder of the process stream and recycling the separated portion to the reactor, with the proviso that no more than about 50 weight percent of the catalyst is separated from the liquid process stream and recycled to the reactor.

15. The process of claim 14 wherein the chlorinating agent is HCl and the reactant is selected from the group consisting of vinyl chloride and ethylene.

16. The process of claim 14 wherein the chlorinating agent is chlorine and the reactant is ethylene.

17. The process of claim 14 wherein the portion of the liquid process stream containing the solid catalyst is separated from the liquid process stream by means of a cyclone.

18. The process of claim 17 wherein the catalyst is FeCl$_3$.

19. The process of claim 17 wherein the chlorinated hydrocarbon is 1,1-dichloroethane produced by the reaction of vinyl chloride and HCl in the presence of a FeCl$_3$ catalyst.

20. The process of claim 18 wherein the portion of the liquid process stream separated from the remainder of the process stream contains at least about 35 weight percent of the catalyst.

21. The process of claim 20 wherein the portion of the liquid process stream separated contains at least about 50 weight percent of the catalyst.

22. The process of claim 14 wherein the catalyst retains at least about 75 percent of its catalytic activity.

23. The process of claim 22 wherein the catalyst retains at least about 90 percent of its catalytic activity.

* * * * *